United States Patent [19]

Maeda et al.

[11] Patent Number: 4,732,933
[45] Date of Patent: Mar. 22, 1988

[54] NEOCARZINOSTATIN COMPLEXES, A METHOD FOR PRODUCING THE SAME, AND AN ANTITUMOR AGENT CONTAINING SAID COMPLEXES AS AN ACTIVE COMPONENT

[75] Inventors: Hiroshi Maeda, 631-3, Aza-Tamukae, Hotakubohon-machi Kumamoto City; Ryunosuke Kanamaru; Nakao Ishida, both of Sendai; Toshihiko Yoshitake, Kurashiki; Minoru Ueda, Okayama, all of Japan

[73] Assignees: Kayaku Antibiotics Research Co., Ltd.; Kuraray Co., Ltd.; Yamanouchi Pharmaceutical Co., Ltd., all of Kurashiki; Hiroshi Maeda, Kumamoto, all of Japan

[21] Appl. No.: 730,823

[22] Filed: May 6, 1985

Related U.S. Application Data

[63] Continuation of Ser. No. 469,235, Feb. 24, 1983, abandoned.

[30] Foreign Application Priority Data

Feb. 27, 1982 [JP] Japan .................................. 57-31558
Jan. 31, 1983 [JP] Japan .................................. 58-15075

[51] Int. Cl.$^4$ ...................... C08L 89/00; A61K 31/785
[52] U.S. Cl. .................................. 525/54.1; 525/327.6; 424/78; 260/DIG. 47

[58] Field of Search .................... 525/54.1, 54.11, 328; 526/238.1; 424/78

[56] References Cited

U.S. PATENT DOCUMENTS

| | | | |
|---|---|---|---|
| 3,085,994 | 4/1963 | Muskat | 526/272 |
| 3,121,043 | 2/1964 | Tobin et al. | 525/327.6 |
| 3,245,933 | 4/1966 | Muskat | 524/388 |
| 4,182,752 | 1/1980 | Maeda et al. | 260/DIG. 47 |

*Primary Examiner*—Delbert R. Phillips
*Assistant Examiner*—Nathan M. Nutter
*Attorney, Agent, or Firm*—Burns, Doane, Swecker & Mathis

[57] ABSTRACT

Novel neocarzinostatin anticancer agents have the formula:

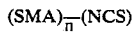

$$(SMA)_{\overline{n}}(NCS)$$

wherein (NCS) is a neocarzinostatin residue, n is an integer ranging from 1 to 35, and (SMA) comprises the residue of a half-esterified styrene-maleic acid copolymer having an average molecular weight of from 1,000 to 10,000, said half-esterified styrene-maleic acid copolymer comprising (i) styrene residues, (ii) maleic acid residues covalently bonded to (NCS), (iii) free maleic acid residues, and (iv) half-esterified maleic acid residues, and further wherein the total amount of said residues (ii) and (iii) ranges from an average of 0.1 per molecule to 60 mole % of said (SMA).

15 Claims, 16 Drawing Figures

FIG_5b

FIG_5c

NEOCARZINOSTATIN COMPLEXES, A METHOD FOR PRODUCING THE SAME, AND AN ANTITUMOR AGENT CONTAINING SAID COMPLEXES AS AN ACTIVE COMPONENT

This application is a continuation of application Ser. No. 469,235, filed Feb. 24, 1983, and now abandoned.

BACKGROUND OF THE INVENTION

1. Field of the Invention

The present invention relates to novel neocarzinostatin complexes, more particularly to neocarzinostatin complexes represented by the following formula (I):

$$(SMA)_n-(NCS) \quad (I)$$

wherein n is an integer of 1–35, NCS represents neocarzinostatin residue, SMA represents a residue of a half esterified styrene-maleic acid copolymer having an average molecular weight of 1,000–10,000 in which the maleic acid portion consists of the following units.

(1) maleic acid residue bonded to NCS (2) maleic acid residue which is free or bound to NCS by non-covalent bonding provided that the total amount of the above described maleic acid residues (1) and (2) is from an average content of 0.1 per molecule to 60 mol % of SMA, and (3) half-esterified maleic acid residue wherein R is a monohydric alcohol residue or a residue of monohydroxyalkyl ether of di- or trihydric alcohol, and a method for producing the same.

Neocarzinostatin is a proteinic anticarcinogen produced in a media in which Streptomyces carzinostaticus var. F-41 Kuroya is cultured (Japanese Patent Publication No. 42 (1967)-21752 and U.S. Pat. No. 3,334,022). With respect to the primary structure of this substance, the total number of amino acid residues and estimated molecular weight have been reported to be 109 and 10,700 respectively, by Hiroshi Maeda who is one of the present inventors (Science, 178, 875–876 (1972) and Arch. Biochem. Biophys., 163, 379–385).

SUMMARY OF THE INVENTION

In the treatment of cancer, the metastasis of cancer cells is important and particularly the metastasis of said cells into lymph nodes is the most important problem. A wide variety of neocarzinostatin derivatives have been examined with the aim of lowering the toxicity and prolonging the activity of medicinal values possessed by neocarzinostatin, and with the aim of directing specific migration to the lymphatic system. As a result, it has been found that neocarzinostatin derivatives obtained by reacting two primary amino groups present in the molecule of neocarzinostatin with a partially hydrolyzed product of a water soluble styrene-maleic acid copolymer, possess the above described activities and this has been disclosed in U.S. Pat. No. 4,182,752.

Furthermore, anticancer agents are desired to have a high affinity to the tumor in addition to the above described delivery of said agents into the lymphatic system in order to prevent the metastasis of cancer. When the affinity of the agent to the tumor is high, the anticancer agent accumulates preferentially at tumor site, thus raises its concentration. This will also results in reducing the side effect in other organs.

The inventors have made a variety of studies and found that neocarzinostatin complexes obtained by reacting neocarzinostatin with half esterified styrene-maleic acid copolymer having maleic anhydride residues and an average molecular weight of 1,000–10,000, which are different from styrene-maleic anhydride copolymers or the partially hydrolyzed products, can attain the above described objects.

DETAILED DESCRIPTION OF THE INVENTION

The present invention lies in neocarzinostatin complexes represented by the following formula (I):

$$(SMA)_n-(NCS) \quad (I)$$

wherein n is an integer of 1–35, NCS represents neocarzinostatin residue, SMA represents a residue of a half-esterified styrene-maleic acid copolymer having an average molecular weight of 1,000–10,000, in which the maleic acid portion consists of the following units.

(1) maleic acid residue bonded to NCS (2) maleic acid residue which is free or bound to NCS by non-covalent bonding provided that the total amount of the above described maleic acid residues (1) and (2) is from an average content of 0.1 per molecule to 60 mol % of SMA, and
(3) half-esterified maleic acid residue wherein R is a monohydric alcohol residue or a residue of monohydroxyalkyl ether of di- or trihydric alcohol, and a method for producing the neocarzinostatin complexes represented by the following formula (I):

$$(SMA)_n—(NCS) \quad (I)$$

wherein n is an integer of 1-35, NCS represents neocarzinostatin residue, SMA represents a residue of a half-esterified styrene-maleic acid copolymer having an average molecular weight of 1,000–10,000 in which the maleic acid portion consists of the following units.
(1) maleic acid residue bonded to NCS (2) maleic acid residue which is free or bound to NCS by non-covalent bonding

−CH−COOH
|
−CH−COOH provided that the total amount of the above described maleic acid residues (1) and (2) is from an average content of 0.1 per molecule to 50 mol % of SMA, and
(3) half-esterified maleic acid residue wherein R is a monohydric alcohol residue or a residue of monohydroxyalkyl ether of di- or trihydric alcohol, which comprises reacting neocarzinostatin with a half-esterified styrene-maleic anhydride copolymer having an average molecular weight of 1,000–10,000 and maleic anhydride residue of from an average content of 0.1 per molecule to 60 mol % of SMA.

Neocarzinostatin complexes (I) according to the present invention have the same useful properties as the above described neocarzinostatin derivatives and are highly soluble in the lipid medium and can be used as an oil soluble composition. When the complexes (I) of the present invention are administered as an oil soluble composition in specific artery, the drug can be accumulated at the tumor site more selectively than other route of administration. Furthermore, it will stay in the tumor for a long period of time, and thus excert the high antitumor activity.

On the other hand, the complexes (I) of the present invention have the water solubility in addition to the lipid solubility, so that said complexes can be applied to the systemic administration by means of a water soluble composition, for example, intravenous injection and the like.

Such desirable improvement of neocarzinostatin owing to the complexes (I) of the present invention is considered to rely upon the use of half-esterified styrene-maleic anhydride copolymers by which the lipid solubility is given to neocarginostatin while maintaining the water solubility.

The present invention is characterized in that when the anticancer is used as an intravenous injection, it moves toward interstitial space from blood capillaries and uniquely migrates to lymphatic systems. When SMANX is used as an oil solution, it will administered via feeding artery and it is deposited in the tumor site either in the capillaries or outside of the capillaries and gradually released.

For this purpose, in order to leak the complex (I) of the present invention into the tumor tissues from the blood capillaries, the molecular weight is preferred to be less than 80,000 and in order to obtain the solubility in an oil base composition and unique delivery to the tumor into the limphatic system, the molecular weight is preferred to be more than 10,000.

After the complex (I) of the present invention reaches to the desired sites in vivo, the said complex directly or after a partial hydrolysis, the neocartinostatin exerts the antitumor activity. The complexes (I) of the present invention can expect the effect that said complexes form polyamino and the immunological system in vivo.

The complexes (I) of the present invention are ones of 1-35 molecules, generally 2-15 molecules of SMA per molecule of NCS. The detail of the bonding form of NCS and SMA is unclear. The structure of NCS has been already clarified in the above described literature [Science, 178, 875–876 (1972)] and according to this publication, only two primary amino groups are present on the peptide chain, that is, alanine at the N-terminal and lysine at the twentieth position from the N-terminal, so that in the reaction of NCS with SMA, two primary amino groups of NCS can react with maleic anhydride residues of SMA. Furthermore, NCS has a large number of secondary amino groups, hydroxyl groups and the like, so that it is considered that there may be some kind of secondary bonds on account of some kind of intermolecular forces between above mentioned functional groups and SMA by which the complexes of the above described formula (I) are formed.

Thus, it is considered that the complexes of the present invention include ones in which either one of two primary amino groups of NCS form amide bonds with SMA and furthermore ones in which the above described functional groups form ester and amide bonds. Since the total number of the functional groups of NCS is 35, the content of SMA molecule per molecule of NCS may be 1-35 in the complexes. Practically, one molecule of NCS may bind with 2-15 molecules of SMA to form the complex.

SMA to be used in the present invention consists of the following main chain units, that is, maleic acid half ester residue styrene residue and maleic anhydride residue The SMA has a molecular weight of 1,000–10,000 and can be easily produced by half-esterifying styrene-maleic anhydride copolymers with mono-alcohols mentioned below following to usual processes. In the above formula, R is (1) a linear lower alkyl residue having 1-5 carbon atoms, such as methyl, ethyl, propyl, butyl, pentyl, etc., preferably normal alkyl groups, more particularly n-butyl, or monohydroxy-alkyl ether residues of di- or trihydric alcohols, for example (2) alkylene glycol mono-lower alkyl ether residue, wherein the alkylene group is ethylene or butylene and the lower alkyl group has 1–4 carbon atoms and is preferably ethyl or n-butyl, more particularly n-butyl, (3) polyethyleneglycol mono-alkyl ether residue represented by the formula $R'—O—(C_2H_4O)_{\overline{n}}$ wherein R' is a linear alkyl group having 1-8 carbon atoms, $2 \leq n \leq 20$, or (4) glycerin dialkyl ether residue, wherein the alkyl group has 1–4 carbon atoms.

A content of maleic anhydride residue in SMA ranges from 0.1 per molecule to 60 mol %. Maleic anhydride residue must be not less than 0.1 per molecule irrelative to the molecular weight of SMA. The term "0.1 per molecule" of maleic anhydride residue used herein means that one anhydride group is present in ten SMA molecules. The upper limit must be not greater than 60 mol % based on the total content of the anhydride residue of the initial SMA. To show the term "upper limit" more concretely, suppose firstly the molecular weight of SMA to be 1,000, then the content of the anhydride residue must not exceed 3.0 per molecule, and secondly the molecular weight to be 10,000, then said content must not exceed 30 per molecule. The content of the anhydride residue is more preferably from 0.4 per molecule to 50 mol %. As the molecular weight increases, the content of maleic anhydride residue may also increase but if said content is too large, the reaction of maleic anhydride with NCS becomes complicated and an amount of the by-product becomes larger, so that the above described range is preferable. Maleic anhydride residues in SMA which are not reacted with NCS, become its ring opened due to hydrolysis in the course of the reaction to form maleic acid residues. Thus, when the reaction is carried out in an aqueous medium, maleic anhydride residues are substantially not present in SMA residue in the complexes (I) of the present invention. The term "half ester" used herein means that one of the two carboxyl groups attached to a maleic acid formed by opening the ring of maleic anhydride has been esterified and it is preferable that substantially all maleic acid residues other than maleic anhydride residues are half esterified but a part thereof may be free maleic acid residues.

The reaction temperature for producing the complexes of the present invention is generally lower than room temperature, preferably 0°–15° C. When the content of maleic anhydride residue in SMA is equal or greater than one per molecule, the products having complicated cross-linking structure may be produced, so that the reaction should be carried out at lower temperatures, such as, lower than 10° C.

The reaction of NCS with SMA is one between polyfunctional polymers, so that it is impossible to specify the reaction sites of the reaction products and to apparently show the molecular structure. But, the analysis of mean structure of the reaction products can be made by the following experimental methods, such as, electrophoresis, gel permeation chromatography, gel filtration, infrared absorption spectrum, ultraviolet absorption spectrum and elemental analysis and the like.

Neocarzinostatin complexes (I) of the present invention can be produced by reacting NCS with SMA. The reaction is generally carried out as follows. NCS is dissolved in an aqueous solution of sodium bicarbonate and then powdery SMA is added thereto while stirring at room temperature or under cooling, preferably at a temperature lower than 15° C. with SMA at equimolar or more, preferably three or more molar excess to NCS. Alternatively, the complexes (I) of the present invention can be produced by mixing SMA solution in a water soluble organi solvent innert to maleic anhydride (for example acetonitrile, dioxane or tetrahydrofurane) and NCS dissolved in an aqueous solution of sodium bicarbonate. After an appropriate period of time, the solvent is removed by evaporation under a reduced pressure. It is considered that the complexes (I) of the present invention are produced by opening the ring of maleic anhydride residue and then reacting with the functional groups of NCS and 1-35 molecules of SMA can react with one molecule of NCS to form the complex but presumably 2-15 molecules of SMA generally react with NCS to form the complex.

Accordingly, the formed complexes include not only the reaction products wherein one or two of two primary amino groups in NCS are reacted with SMA to form amide bonds but also SMA may be reacted with the other functional groups of NCS to form different types of bonds. Complex (I) may be formed by non-covalent bonding between styrene and side chain aromatic hydrophobic ring in NCS as well as ionic bonding between carboxyl groups of SMA and positive charge of NCS such as that of alginine. The above described reaction is carried out by dissolving NCS in an aqueous solution of sodium bicarbonate and adding SMA in the resulting solution but various salts resulting from sodium bicarbonate and an excessive SMA and the like are contained in the reaction product due to the use of such a system, so that these substances are removed by a variety of means, such as dialysis, gel filtration, etc.

The neocarzinostatin complexes (I) of the present invention can be submitted to practical use as medicaments in human therapy by local administration, such as the primary site of cancer and the area of tumor removal or resection, or by intracutaneous, subcutaneous, intramuscular, intravenous, intraarterial and oral administration, or by external application, such as applying or spraying to local site to be treated, suppository, intravesical instillation. The dosages depend on administration routes, malignancy stage and grade of tumor, types of tumor, and conditions of patients. Further, the dosages depend on the purposes, such as the prevention of metastasis to lymph nodes after operation, or therapeutic treatment. The complexes (I) of the present invention are preferably administered in a dosage of 0.01–10 mg/kg once a day for a period of week, or once or twice a week, or on consecutive days. For local application as ointments or for oral administration, the dosage may be further increased.

The complexes (I) of the present invention can be suspended and solubilized in an X-ray oily contrast media of Lipiodol (Ethiodol) (Made by Laboratories André Guerbet (Paris, France), Lipiodol Ultra-Fluide: Fatty acid ethyl ester of iodized poppy seed oil, iodine content: 38 W/W) under ultrasonic wave. When an oil of the complex (I) of the present invention having 1–2 mg/1 ml of Lipiodol is applied in intraarterial administration, Lipiodol and the present complex stay in blood vessel selectively at tumor for a long period of time, so that the high antitumor activity is developed. By dissolving the complex (I) in Lipiodol, the size and local of the tumor, can be observed by X-ray, and tomogram can be followed effectively even after one month.

The use of the complexes (I) in such an oil form is one characteristic applying process for utilizing the properties of the complexes.

The complexes (I) of the present invention are dissolved in 1–9% of aqueous sodium bicarbonate solution or alike. When this aqueous solution is applied in intravenous administration, said medicine accumulates in lymph. This will result in as antimetastatic effect in lymphatic system.

The use of the complexes in the form of such an aqueous salt solution is one characteristic applying process for utilizing the properties of the complexes (I) of the present invention.

The following examples are given for the purpose of illustration of the present invention and are not intended as limitations thereof.

REFERENCE EXAMPLE 1

(a) To 176 ml of p-cymene previously heated to 132°–134° C. under stirring was added continuously and dropwise for 3 hours a solution of 29.4 g of maleic anhydride, 30.9 g of styrene and 1 g of benzoyl peroxide in 200 g of p-cymene. A polymerization reaction occurred concurrently with the addition of the solution, and white turbide precipitate of styrene-maleic anhydride copolymer was formed. After completion of the polymerization reaction, the precipitate was filtered, washed and dried to obtain 58 g of a white powdery styrene-maleic anhydride copolymer.

The resulting styrene-maleic anhydride copolymer was deduced to be an alternate copolymer from the polymerizability of each monomer, and this structure was supported by the result of elemental analysis as well. A number average molecular weight of this copolymer was determined by using acetonitride as a solvent through a vapor pressure osmometry by means of a VPO apparatus made by KNAUER Co. and said value was 1760.

(b) In 40 ml of dioxane was dissolved 20 g of the above obtained styrene-maleic anhydride copolymer, and then 12 ml of n-butanol and 0.2 g of lithium acetate were added thereto. The resulting mixture was charged in a test tube. After the test tube was sealed, a polymerization reaction was effected at 90° C. and 25 hours. After completion of the reaction, the reaction solution was dried under a reduced pressure to evaporate and remove the solvent from the reaction solution. The resulting residue was washed with a mixture of n-hexane and acetone (volume ratio of 9:1), and then dried under a reduced pressure to obtain a light yellow half butyl-esterified styrene-maleic anhydride copolymer wherein maleic anhydride rings have been partially remained. The molecular weight was measured by the vapor pressure osmometry to obtain 2,200, and an averge maleic anhydride ring content was calculated to be 0.75/molecular from the ratio of $D_{1,780}/D_{700}$ of the infrared absorption spectrum.

Elemental analysis value: C: 67.29; %, H: 6.83% and N: 0.19% (Observed).

EXAMPLE 1

In 80 ml of a 0.5M aqueous solution of sodium bicarbonate was dissolved 0.2 g of neocarzinostatin, and then 0.9 g of powder of the half butyl-esterified styrene-maleic anhydride copolymer having a number average molecular weight of 2,200 and an average maleic anhydride ring content of 0.75/molecule, which has been obtained in the above Reference example 1, was added four times thereto at room temperature under stirring at intervals of 20 minutes. After the half butyl-esterified styrene-maleic anhydride copolymer powder was completely dissolved in the aqueous sodium bicarbonate solution, a stirring was further continued for 40 minutes. The reaction solution was charged into a dialysis tube (Union Carbide Co., Chicago), and subjected to a dialysis in a 5 mM aqueous solution of sodium bicarbonate under pressure. After the dialysis at 4° C. for 2 days exchanging several times of the 5 mM aqueous solution of sodium bicarbonate, a dialysis was further continued for 2 days in a 5 mM aqueous solution of sodium bicarbonate kept at 4° C., and then for 2 days in a 1.25 mM aqueous solution of ammonium bicarbonate kept at 4° C. The reaction mixture after the dialysis was freeze-dried, and then the dried material was repeatedly subjected to three times of the operations of suspension in pure water, washing and collection of insoluble part by a centrifugal separator. The above treated material was freeze-dried to obtain 0.15 g of a white fluffy solid of neocarzinostatin-half butyl-esterified styrene-maleic acid copolymer complex (SMANX). The resulting SMANX has the following elemental analysis value.

C: 60.52%, H: 6.48% and N: 3.33% (Observed).

Figure 1:
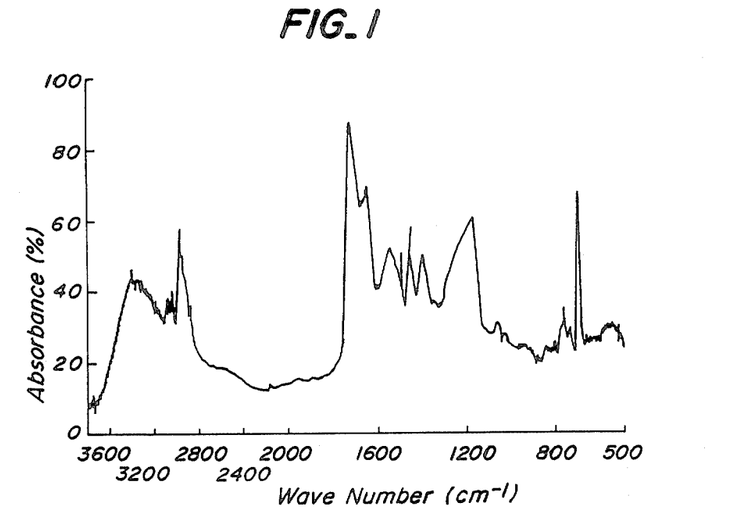
FIG. 1 shows an infrared absorption spectrum of neocarzinostatin-half butyl-esterified styrene-maleic acid copolymer complex (hereinafter abbreviated as SMANX) according to the present invention obtained in Example 1.
Figure 2:
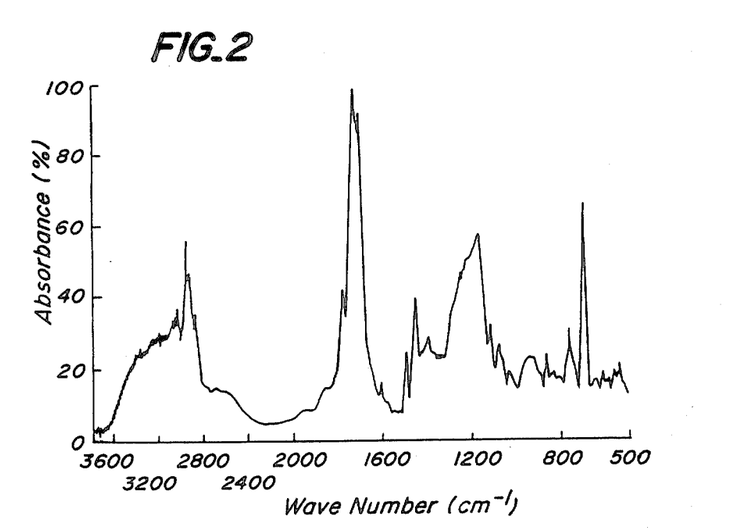
FIG. 2 shows an infrared absorption spectrum of half butyl-esterified styrene-maleic anhydride copolymer used in Example 1.
Figure 3:
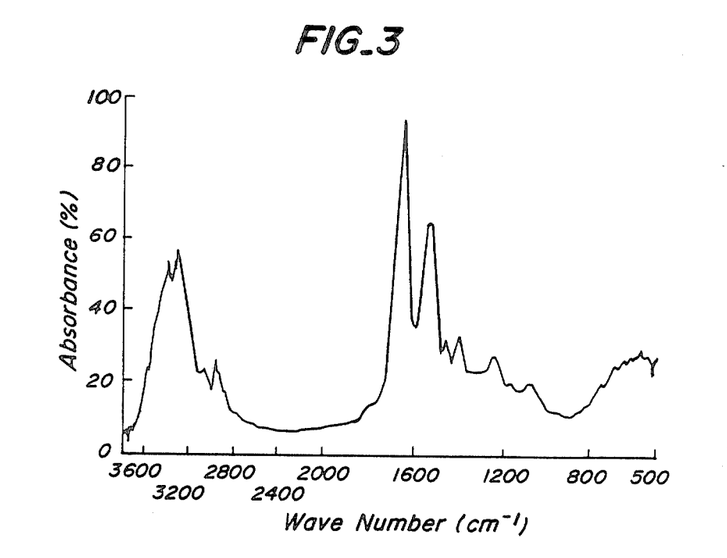
FIG. 3 shows an infrared absorption spectrum of neocarzinostatin used in Example 1.
Figure 4A:
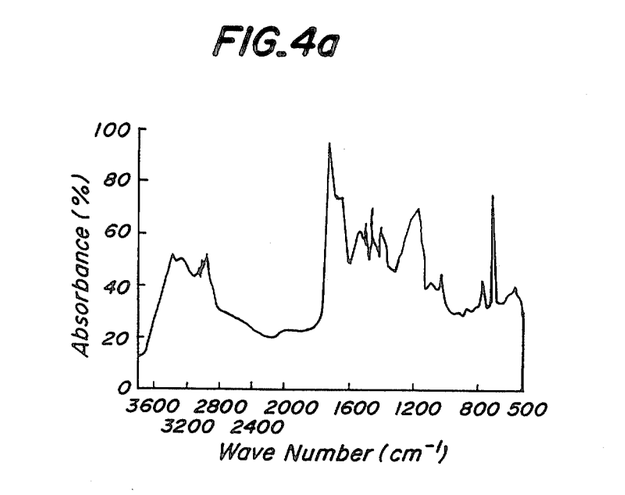
FIGS. 4a–4d show infrared absorption spectra of SMANX according to the present invention obtained in Examples 2–5, respectively.
Figure 4B:
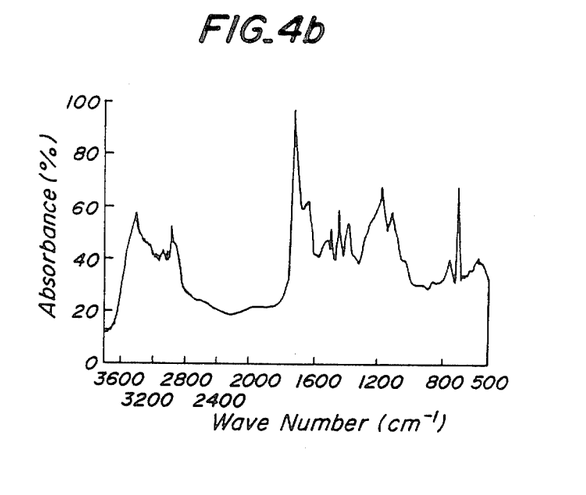
Figure 4C:
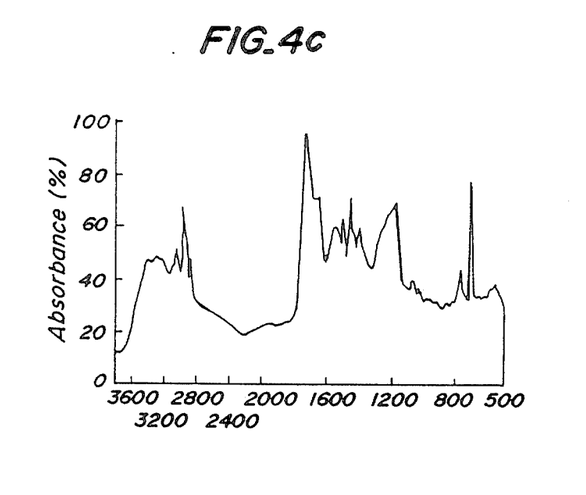
Figure 4D:
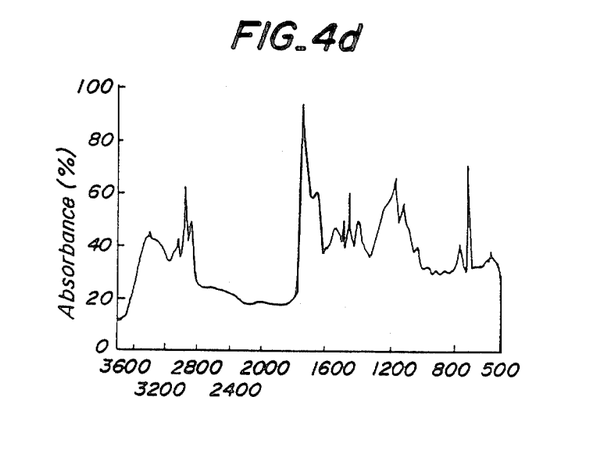
Figure 5A:
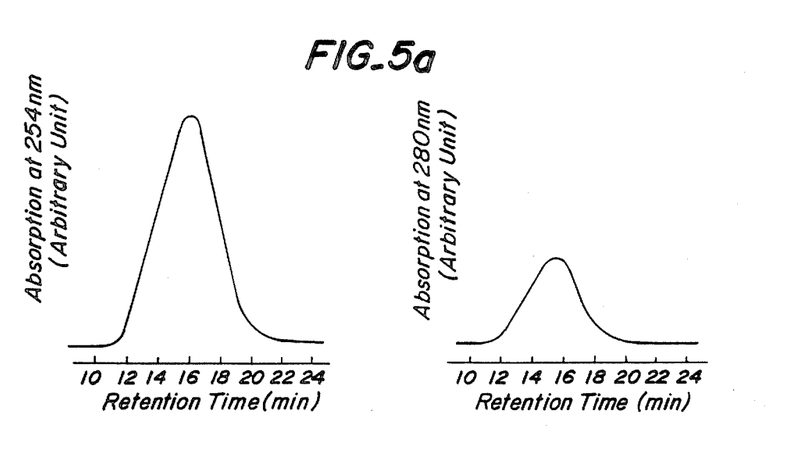
FIGS. 5a–5d show gel permeation chromatograms of SMANX according to the present invention obtained in Examples 2–5, respectively.
Figure 5B:
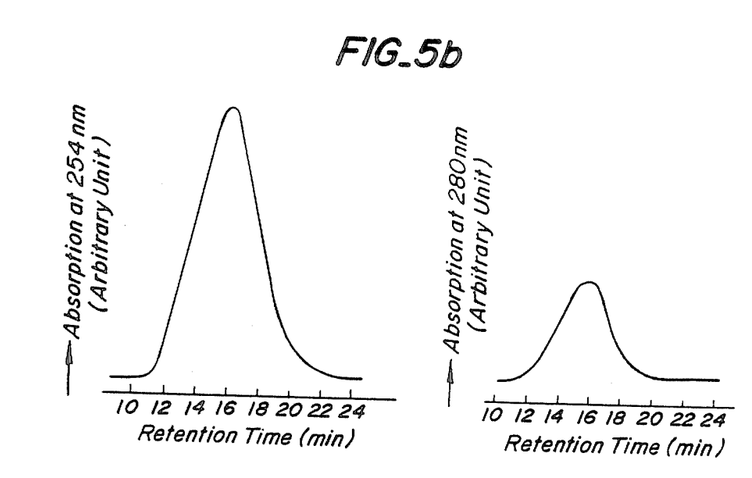
Figure 5C:
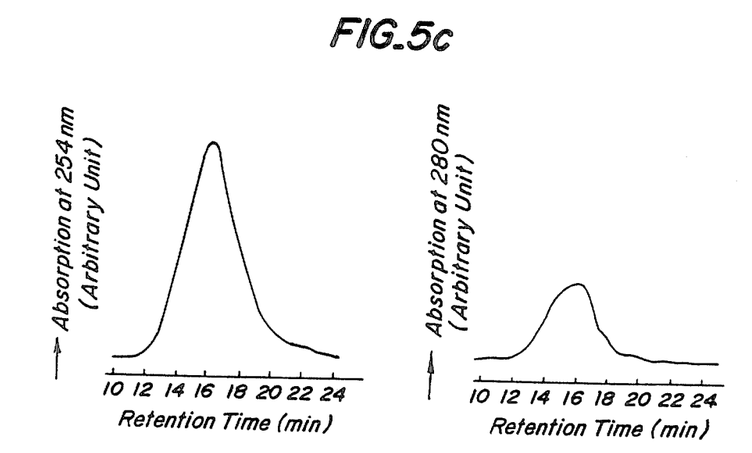
Figure 5D:
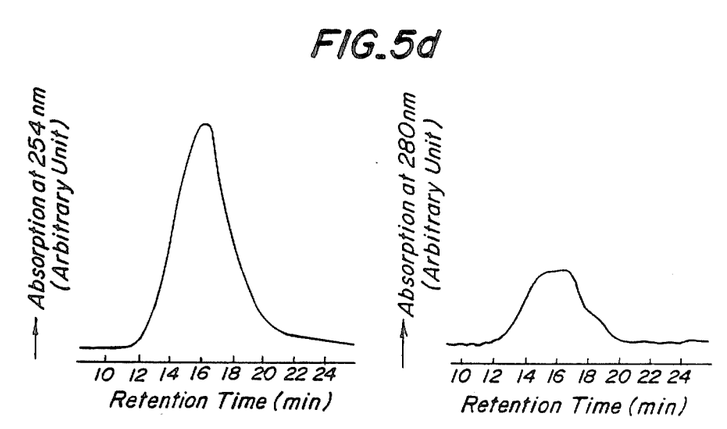

The infrared absorption spectrum (in KBr) of the resulting SMANX is shown in FIG. 1, and the infrared absorption spectra (in KBr) of the half butyl-esterified styrene-maleic anhydride copolymer are shown in FIGS. 2 and 3, respectively. The SMANX exhibited a molecular weight of about 43,000 as measured by polyacrylamide gel disc electrophoresis with sodium dodecyl sulfate (SDS) MANX softens slightly at 230° C. and begins to decompose at 250° C.

The solubility of SMANX in various solvents is shown in the following Table 1 and compared with NCS and the half butyl-esterified styrene-maleic anhydride copolymer used as the starting materials.

TABLE 1

(concentration: 1 mg/ml)

| Solvent | SMANX | NCS | Half butyl-esterified styrene-maleic anhydride copolymer |
|---|---|---|---|
| 10 mM aqueous solution of sodium bicarbonate | soluble | soluble | soluble |
| Methanol | soluble | insoluble | soluble |
| Pyridine | soluble | insoluble | soluble |
| Acetone | swell | insoluble | soluble |
| Dioxane | swell | insoluble | soluble |
| Water pH 5.0 | insoluble | soluble | insoluble |
| pH 8.0 | soluble | soluble | insoluble |
| Lipiodol | soluble | insoluble | insoluble |

It can be seen from Table 1 that SMANX is different from both NCS and half butyl-esterified styrene-maleic anhydride copolymer, but it is a unique entity.

REFERENCE EXAMPLE 2

Into a test tube were added 10 g (0.0048 mole) of a styrene-maleic anhydride copolymer having a number average molecular weight of 2,100 as measured by the vapor pressure osmometry, 0.1 g of lithium acetate and a given amount of each of alcohol and dioxane, and after the test tube was fused to seal shaken for 24 hours at room temperature. The homogeneous solution was heated at 90° C. for 15 hours and then cooled to room temperature. The reaction solution was taken out from the test tube, diluted with dioxane into 2 times of the original volume, and then freeze-dried. The dried material was further dried at 60° C. for 24 hours in vacuo and light yellow flaky product (SMA) was obtained wherein maleic anhydride rings have been partially retained. Half of all the remaining carboxyl were the half-esterified SMA. The amount of anhydride residue remained in the resulting SMA was quatitatively analyzed from the ratio in the optical densities at wave numbers of 1,780 cm$^{-1}$ and 700 cm$^{-1}$ by the infrared absorption spectrum method. The type and amount of alcohols and dioxane, the average molecular weight of the resulting SMA measured by the vapor pressure osmometry and the content of anhydride component remained in the SMA are shown in the Table 2.

TABLE 2

| Alcohol | | Volume of dioxane (ml) | Obtained SMA | | |
|---|---|---|---|---|---|
| Kind | Amount (mole) | | Molecular weight | mol % of maleic anhydride | Moles of anhydride per mole of SMA |
| Ethanol | 0.044 | 25 | 2,260 | 26 | 2.6 |
| Ethyle cellosolve | 0.082 | 20 | 2,330 | 25 | 2.5 |
| n-Butanol | 0.038 | 25 | 2,280 | 28 | 2.8 |
| n-Butyl cellosolve | 0.057 | 20 | 2,510 | 28 | 2.8 |

EXAMPLES 2-5

In 50 ml of chilled 0.5M sodium bicarbonate 0.5 g of NCS was dissolved in dark. Then, 3.0 g of each of the SMA powder described in Table 2 were added in several divided portions to the above solution, and the resulting mixture was thoroughly stirred until SMA was completely dissolved in the solution. After a homogeneous solution was formed, the solution was left to stand for 16 hours at 4°-6° C. During the reaction, the pH of the reaction mixture was kept within 8.3 to 8.7. Then, the reaction solution was transfered to a dialysis tube, and dialyzed in 1 l of a 10 mM of ammonium bicarbonate at 4°-6° C. for 3 days under pressure, with several changes of the dialyzing solution. Then te dialysate was lyophilized and white fluffy SMANX powder was obtained. With respect to SMANX complexes showed molecular weight about 57,000, 56,000, 40,000 and 65,000 as measured by SDS disc gel electrophoresis and elemental analysis respectively.

The rate of reaction (mol %) of the primary amino group was determined and the results are shown in Table 3.

TABLE 3

| Experiment No. | Alcohol for esterification | Reaction of primary amino group (mol %) | Yield of SMANX (wt. %) |
|---|---|---|---|
| Example 2 (a) | Ethanol | 83.3 | 70.2 |
| Example 3 (b) | Ethyl cellosolve | 77.3 | 72.6 |
| Example 4 (c) | n-Butanol | 71.7 | 76.2 |
| Example 5 (d) | Butyl cellosolve | 61.0 | 68.5 |

TABLE 4

| Experiment No. | Results of elemental analysis (wt. %) | | |
|---|---|---|---|
| | N | C | H |
| Example 2 | 2.42 | 60.17 | 6.07 |
| Example 3 | 2.42 | 57.18 | 6.17 |
| Example 4 | 3.42 | 60.51 | 6.36 |
| Example 5 | 2.08 | 61.93 | 6.96 |

Figure 6:
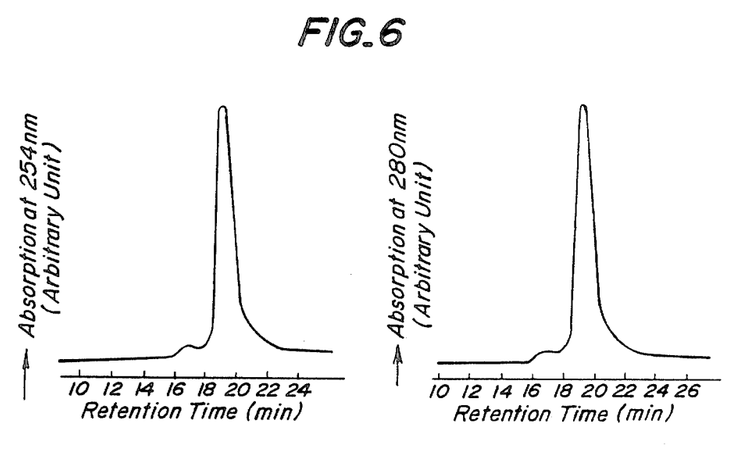
FIG. 6 shows a gel permeation chromatogram of neocarzinostatin used in Examples 2–5.
Figure 7A:
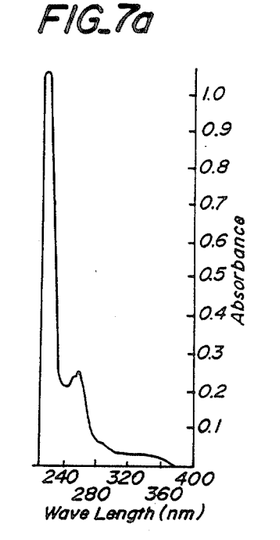
FIGS. 7a–7d show ultraviolet and visible ray absorption spectra of SMANX according to the present invention obtained in Examples 2–5, respectively.
Figure 7B:
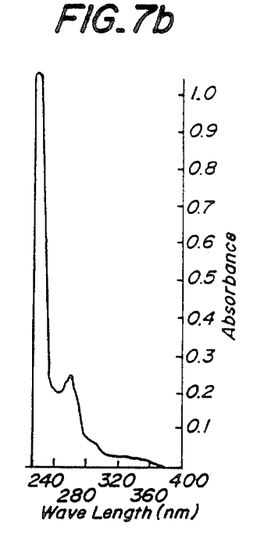
Figure 7C:
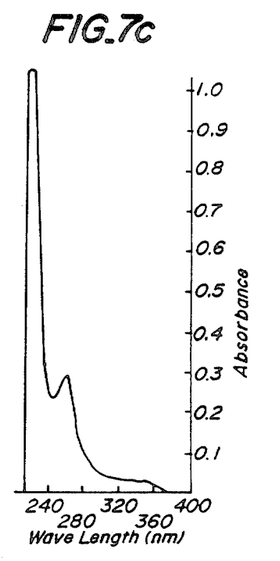
Figure 7D:
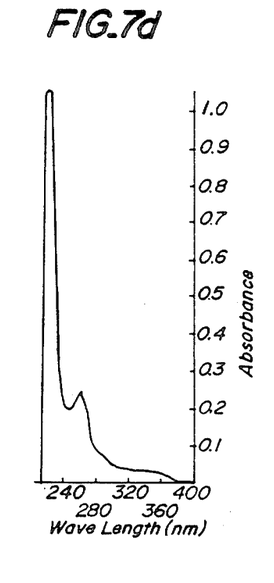

The amount of the residual free amino group of the complexes according to the present invention was measured as follows. An aliquot of the solution after completion of the reaction was diluted with water, then the primary amino group was reacted with tri-nitrobenzene sulfonic acid, and the amount of the resulting nitrobenzene derivative was determined by spectrophotometer. Results of elemental analysis of the resulting complexes are shown in Table 4. Infrared absorption spectra of the complexes measured by the KBr tablet method are shown in FIGS. 4a–4d. FIGS. 5a–5d show gel permeation chromatograms of the complexes measured at a pH of 7.9 by using a G-3000 SW column made by Toyo Soda Co. and further using a 10 mM aqueous solution of ammonium bicarbonate as a mobile phase. For comparison, FIG. 6 shows a gel permeation chromatogram of NCS. FIGS. 7a–7d show ultraviolet and visible ray absorption spectra of the complexes in a 0.5M sodium bicarbonate. Furthermore, the solubility of the complexes in various solvents is shown in Table 5.

TABLE 5

| Samples type of SMA ester | Solubility of complex (2 mg/1 ml) | | | | |
|---|---|---|---|---|---|
| | Aqueous solution of sodium bicarbonate (10 mM) | Water | Pyridine | Acetone | Dioxane |
| Ethyl | +++ | + | ++ | ++ | ++ |
| Ethyl-cellosolve | +++ | + | ++ | ++ | ++ |
| n-butyl | +++ | + | ++ | ++ | ++ |
| n-butyl-cellosolve | +++ | + | ++ | ++ | ++ |

+++: very soluble, ++: soluble, +: slightly soluble.

EXAMPLE 6

By effecting the reaction under the same conditions as in Reference example 2 except for using styrene-maleic anhydride copolymer having a number average molecular weight of 1,760, partially butyl-esterified styrene-maleic anhydride copolymer having an average number of maleic anhydride residue of 2.1 per molecule and an esterification degree of 72 mol % (total amount of maleic acid residue of 28 mol %) was obtained. 0.5 g of neocarzinostatin was dissolved in 100 ml of a 0.5M aqueous solution of sodium bicarbonate at a temperature of 5°–8° C. under dark and 2.0 g of the above described partially butyl-esterified styrene-maleic anhydride copolymer was added thereto in several lots by 3 hours while stirring and the mixture was thoroughly stirred until the copolymer was completely dissolved. After the dissolution, the reaction mixture was left to stand at a temperature of 4°–6° C. for 16 hours and the subsequent operation was followed to Examples 2–5 and the reaction product was finally freeze-dried to obtain white fluffy SMANCS complex. In this case, the reaction percentage of amino group was 50.5 mol % and the yield of the complex was 72.9%. The molecular weight estimated by SDS disc gel electrophoresis was 36,000 and the elemental analytical value was as follows.

N: 4.07 wt % C: 59.28 wt % H: 6.18 wt %

The pharmacological activity of the thus obtained SMANCS complex was as follows.

Antitumor test:
1. Compound to be tested:
   SMANCS complex
2. Used animal:
   Male ICR-JCL mouse (6–7 week age),
   body weight: 24–30 g
   1 group: 10 mice
3. Tumor:
   Sarcoma 180 (ascites type)
4. Method:
   0.5 ml ($2 \times 10^6$ cell/ml) of tumor cells pure-cultured in a mouse abdominal cavity for 6–8 days was implanted into abdominal cavity of a mouse. 24 hours after the implantation, SMANCS complex to be tested was intraperitoneal-administered once a day subsequently for 5 days and life and death were observed over 65 days after implantation of the tumor and the surviving percentage was determined from the following formula based on the survived day number.

Surviving percentage =

$$\frac{\begin{pmatrix}\text{average survived day number of}\\ \text{the group administered with}\\ \text{the test compound}\end{pmatrix} - \begin{pmatrix}\text{average survived}\\ \text{day number of}\\ \text{the control group}\end{pmatrix}}{\begin{matrix}\text{average survived day number}\\ \text{of the control group}\end{matrix}} \times 100$$

5. Results

TABLE 6

| Test compound | Dosage (mg/kg) | Administered route | Observed period (day) | Number of mice survived after 60 days | Number of survived day (Average ± S.D.) | Surviving percentage (%) |
|---|---|---|---|---|---|---|
| Control | | | | 0/10 | 12.2 ± 3.4 | |
| | 0.25 | i.p. | 60 | 1/10 | >33.2 ± 11.9** | >172 |
| | 0.5 | | | 0/10 | 36.8 ± 8.8** | 202 |
| | 1 | | | 3/10 | >44.1 ± 13.8** | >261 |
| SMANCS complex | 0.25 | s.c. | | 0/10 | 15.1 ± 7.2 | 24 |
| | 0.5 | | | 0/10 | 16.0 ± 7.4 | 31 |
| | 1 | | | 1/10 | >19.8 ± 16.1 | >62 |
| Control | | | | 0/10 | 12.4 ± 2.5 | |
| | 0.025 | i.p. | 60 | 0/10 | 10.7 ± 8.2** | 67 |
| | 0.05 | | | 0/10 | 22.3 ± 9.8** | 80 |
| | 0.1 | | | 0/10 | 25.9 ± 9.1** | 109 |
| SMANCS complex | 2 | s.c. | | 1/10 | >24.8 ± 16.6** | 103 |

*Significant activity as compared with the control group PL < 0.05
**Significant activity as compared with the control group PL < 0.01

As seen from the above data, in the intraperitoneal (i.p.) administration, the dosage of at least 0.025 mg/kg apparently shows the surviving activity and in the subcutaneous (s.c.) administration, the dosage of 0.25–1 mg/kg is low in the activity and 2 mg/kg shows the apparent surviving activity.

TABLE 7

Tumor affinity in cancer VX-2 of liver of rabit after intravenous injection of SMANX

| | SMANX | 10 mg/kg NCS | | |
|---|---|---|---|---|
| | 90' | 15' | 60' | 90' |
| Interior of tumor | 0.7 | 0 | 0 | 0 |
| Periphery of tumor | 0.32 | 0 | 0 | 0 |
| For distant site (normal liver) | <0.32 | 0 | 0 | 0 |

TABLE 8

Comparison of cell toxicity to normal fibroblasts of rabit*

| | Concentration μg/ml | | | | | | |
|---|---|---|---|---|---|---|---|
| Test compound | 10 | 6 | 1.8 | 1.0 | 0.5 | 0.2 | 0.1 |
| Mitomycin C | +++ | | | +++ | | | + |
| NCS** | | | | + | +/± | | − |
| SMANX | ± | − | | − | | − | − |

*Judgement after 3 days
+ ... Intensity of toxicity
− ... No toxicity
**Cf. $LD_{50} = 1.0$ μg/ml

What is claimed is:

1. A neocarzinostatin complex having the following formula:

wherein (NCS) is a neocarzinostatin residue, n is an integer ranging from 1 to 35, and (SMA) comprises the residue of a half-esterified styrene-maleic acid copolymer having an average molecular weight of from 1,000 to 10,000, said half-esterified styrene-maleic acid copolymer comprising (i) styrene residues, (ii) maleic acid residues covalently bonded to (NCS), (iii) free maleic acid residues, and (iv) half-esterified maleic acid residues, and further wherein the total amount of said residues (ii) and (iii) ranges from an average of 0.1 per molecule to 60 mole % of said (SMA).

2. The neocarzinostatin complex as defined by claim 1, said half-esterified maleic acid residues (iv) having the formula:

wherein R is lower alkyl or the residue of a monohydroxyalkyl ether of a di- or trihydric alcohol.

3. The neocarzinostatin complex as defined by claim 2, wherein R is n-butyl.

4. The neocarzinostatin complex as defined by claim 1, having a molecular weight of less than 80,000.

5. The neocarzinostatin complex as defined by claim 4, having a molecular weight of more than 10,000.

6. The neocarzinostatin complex as defined by claim 1, wherein the total amount of said residues (ii) and (iii) ranges from an average of from 0.1 to less than 1 per molecule of said (SMA).

7. The neocarzinostatin complex as defined by claim 1, wherein the total amount of said residues (ii) and (iii) ranges from an average of from 0.1 to 0.8 per molecule of said (SMA).

8. The neocarzinostatin complex as defined by claim 1, wherein the total amount of said residues (ii) and (iii) ranges from an average of 1 per molecule to 60 mole % of said (SMA).

9. The neocarzinostatin complex as defined by claim 1, wherein the total amount of said residues (ii) and (iii) ranges from an average of 0.4 per molecule to 50 mole % of said (SMA).

10. A composition of matter comprising the neocarzinostatin complex as defined by claim 1, and a pharmaceutically acceptable carrier therefor.

11. The composition of matter as defined by claim 10, comprising a pharmaceutically acceptable lipid carrier therefor.

12. The composition of matter as defined by claim 10, comprising a pharmaceutically acceptable aqueous carrier therefor.

13. The composition of matter as defined by claim 10, further comprising an X-ray contrast medium.

14. A method for the treatment of cancer in a mammalian organism in need of such treatment, comprising administering thereto an anticancer effective amount of the neocarzinostatin complex as defined by claim 1.

15. A method for the treatment of cancer in a mammalian organism in need of such treatment, comprising administering thereto an anticancer effective amount of the composition of matter as defined by claim 10.

* * * * *

UNITED STATES PATENT AND TRADEMARK OFFICE
CERTIFICATE OF CORRECTION

PATENT NO. : 4,732,933

DATED : March 22, 1988

INVENTOR(S) : Hiroshi Maeda et al.

It is certified that error appears in the above-identified patent and that said Letters Patent is hereby corrected as shown below:

On the title page,

[30] Foreign Application Priority Data

Feb. 27, 1982 [JP] Japan ..... change "57-31558" to

--57-31555--

Signed and Sealed this

Twentieth Day of December, 1988

Attest:

DONALD J. QUIGG

Attesting Officer

Commissioner of Patents and Trademarks